(12) United States Patent
Gershkovich et al.

(10) Patent No.: US 8,789,853 B2
(45) Date of Patent: Jul. 29, 2014

(54) MECHANICAL PIPE FITTING DEVICE ASSEMBLY

(75) Inventors: Yefim Gershkovich, Tiberias (IL); Evgeny Nayman, Afula (IL); Tanyana Kogan, Afula (IL)

(73) Assignee: Plassim Fittings Ltd., Kibbutz Merhavia (IL)

( * ) Notice: Subject to any disclaimer, the term of this patent is extended or adjusted under 35 U.S.C. 154(b) by 257 days.

(21) Appl. No.: 12/936,302

(22) PCT Filed: Jan. 20, 2009

(86) PCT No.: PCT/IL2009/000079
§ 371 (c)(1),
(2), (4) Date: Oct. 4, 2010

(87) PCT Pub. No.: WO2009/122391
PCT Pub. Date: Oct. 8, 2009

(65) Prior Publication Data
US 2011/0042943 A1 Feb. 24, 2011

Related U.S. Application Data

(60) Provisional application No. 61/041,940, filed on Apr. 3, 2008.

(51) Int. Cl.
*F16L 33/00* (2006.01)
(52) U.S. Cl.
USPC ............................ 285/249; 285/255; 285/339
(58) Field of Classification Search
USPC ............... 285/339, 322–324, 249, 255, 332.1
See application file for complete search history.

(56) References Cited

U.S. PATENT DOCUMENTS

| 4,775,171 | A | * | 10/1988 | Marshall | 285/101 |
| 4,984,826 | A | * | 1/1991 | Yokomatsu et al. | 285/101 |
| 5,112,087 | A | * | 5/1992 | Haruki | 285/101 |
| 5,150,924 | A | * | 9/1992 | Yokomatsu et al. | 285/101 |
| 5,150,925 | A | * | 9/1992 | Yokomatsu et al. | 285/101 |
| 7,137,654 | B2 | * | 11/2006 | Segal et al. | 285/330 |
| 7,140,618 | B2 | * | 11/2006 | Valls, Jr. | 277/609 |
| 7,404,581 | B2 | * | 7/2008 | Baving et al. | 285/242 |

(Continued)

FOREIGN PATENT DOCUMENTS

| DE | 19654435 A1 | 7/1998 |
| DE | 10212735 A1 | 10/2003 |
| EP | 0 310 234 A | 4/1989 |
| WO | WO 2006/135227 A | 12/2006 |

*Primary Examiner* — James Hewitt
*Assistant Examiner* — Jay R Ripley
(74) *Attorney, Agent, or Firm* — Arent Fox LLP

(57) ABSTRACT

Push-fit pipe fitting device assemblies having a) a main body comprising one or more tubular portions, a first end of each of the tubular portions is connected either to a first end of another tubular portion or to another push-fit pipe fitting device assembly; and each of second ends of the tubular portions is configured to host a pipe; b) one or more tubular inserts, wherein the one or more tubular inserts are fittingly disposed inside tubular portions of the main body; c) one or more nuts, the one or more nuts is fittingly disposed over second ends of the main body; d) one or more grip rings, wherein the one or more grip are fittingly disposed over second ends of the tubular inserts, and inside the one or more nuts; and e) one or more elastomeric sealing rings disposed at each end of the one or more tubular inserts.

18 Claims, 15 Drawing Sheets

CROSS SECTION AA'

(56) References Cited

U.S. PATENT DOCUMENTS

| | | | |
|---|---|---|---|
| 7,611,172 B2 * | 11/2009 | Baving et al. | 285/340 |
| 2002/0163191 A1 * | 11/2002 | Muenster et al. | 285/331 |
| 2005/0035597 A1 * | 2/2005 | Bamberger et al. | 285/340 |
| 2005/0264005 A1 * | 12/2005 | Norman | 285/249 |
| 2007/0001454 A1 * | 1/2007 | Baving et al. | 285/322 |

* cited by examiner

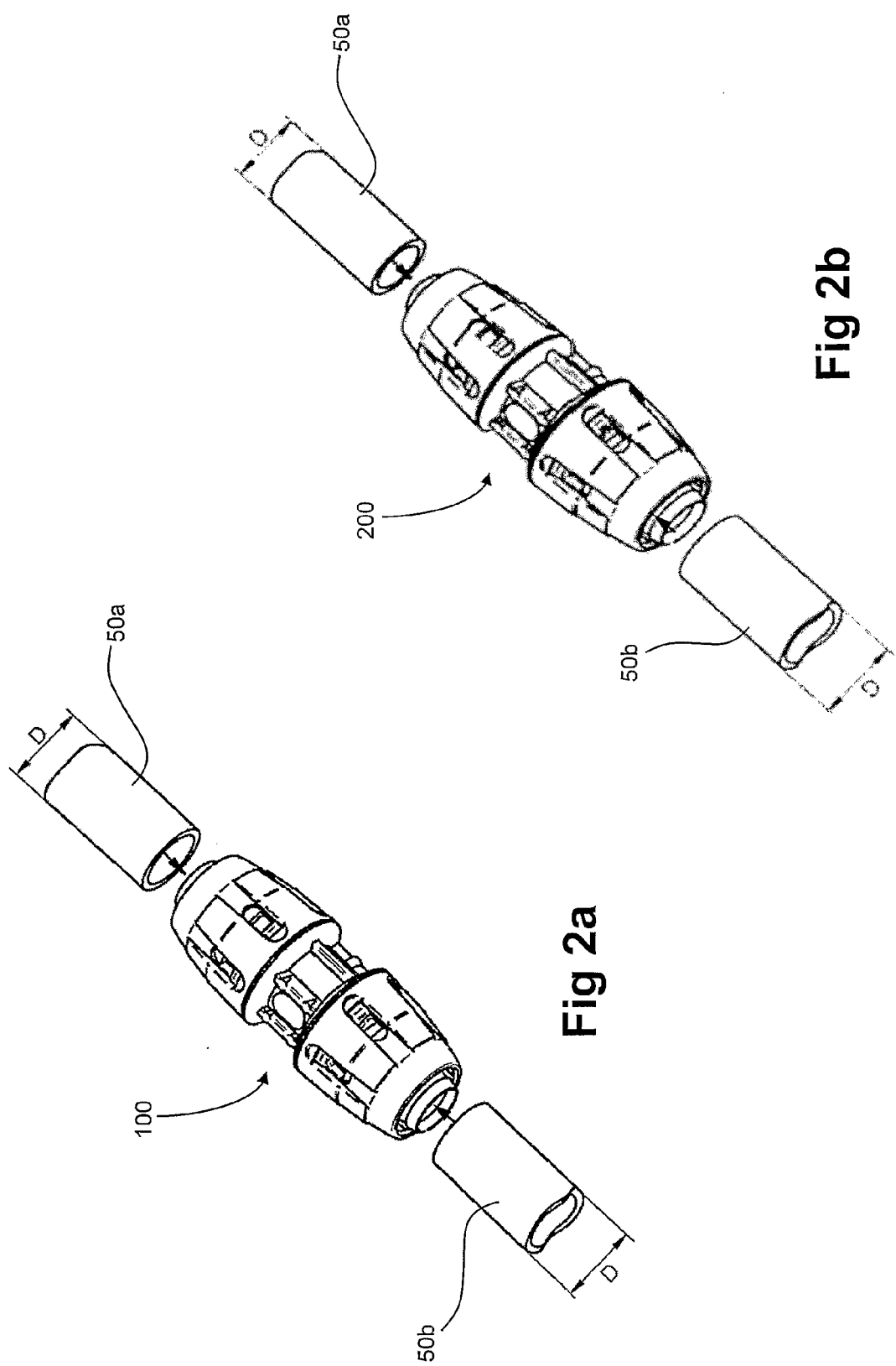

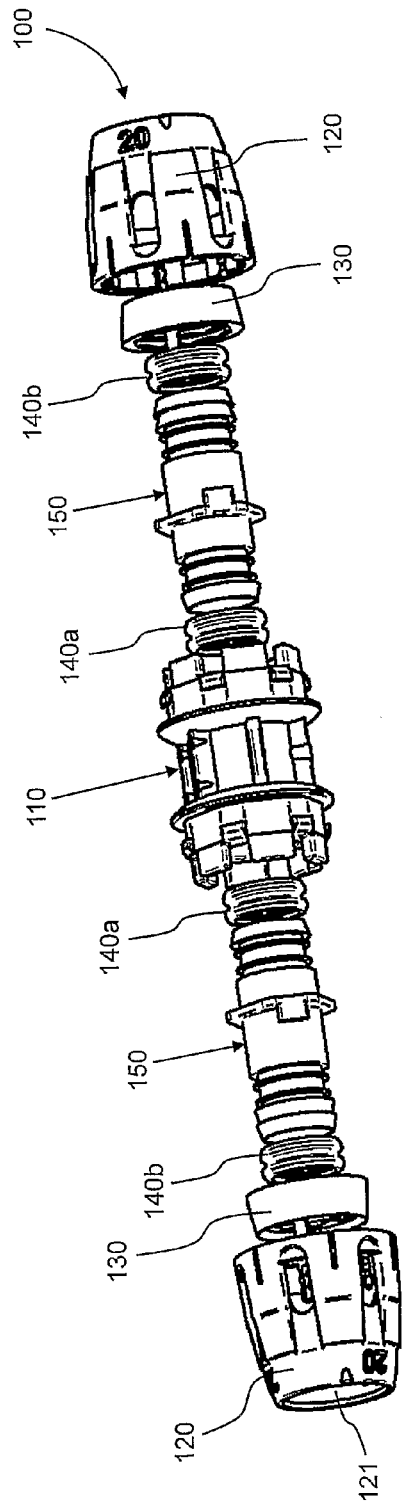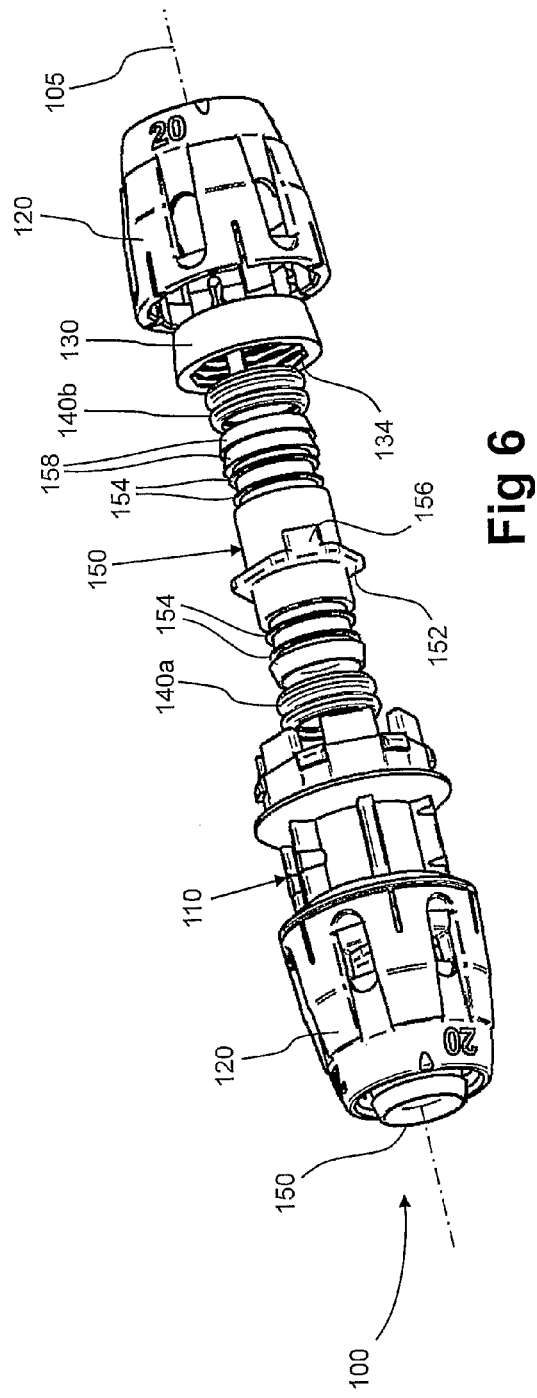

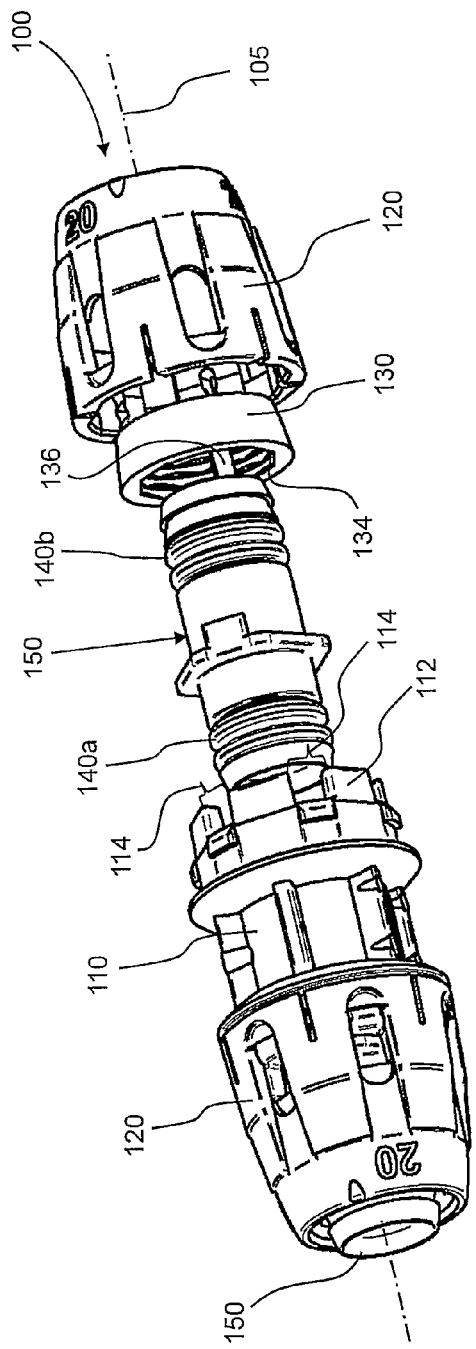
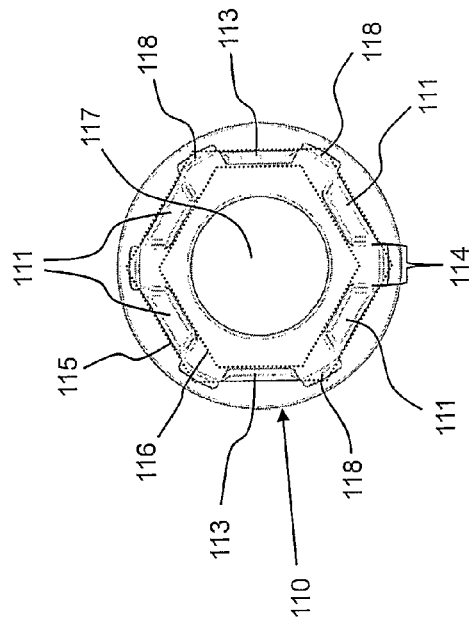
Fig 7
Fig 8

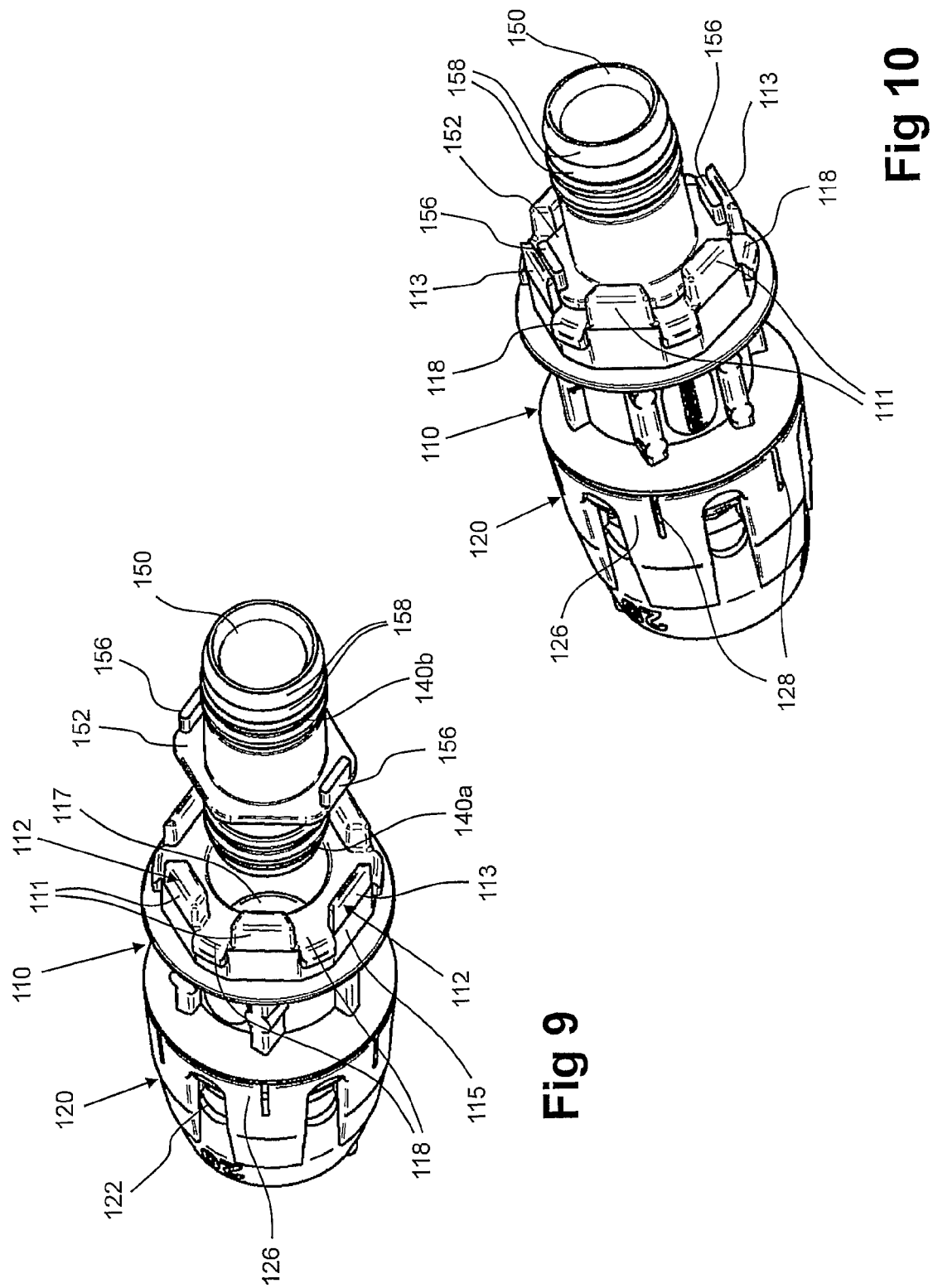

CROSS SECTION AA'

DETAILED A

MECHANICAL PIPE FITTING DEVICE ASSEMBLY

CROSS-REFERENCE TO RELATED APPLICATION

This application is a National Stage entry of International Application No. PCT/IL2009/000079 filed Jan. 20, 2009, which claims priority to U.S. Provisional Patent Application Ser. No. 61/041,490, filed Apr. 3, 2008, the disclosure of the prior applications is hereby incorporated in its entirety by reference.

The unique grip ring is described in PCT application PCT/IL2008/001480, filed Nov. 1, 2008, by Gershkovich et al, the disclosure of which is included herein by reference for all purposes as if entirely set forth herein. The grip ring enables a quick plug-in of a push-fit pipe into a fitting device.

FIELD OF THE INVENTION

This invention relates to grip rings for mechanical pipe fitting (coupling) devices and more particularly the present invention relates to mechanical push-fit pipe fitting device assemblies utilizing unique grip ring, pipe insert and a ring sealer.

BACKGROUND OF THE INVENTION AND PRIOR ART

A plug-in pipe fitting device assembly, also referred to as a push-fit pipe fitting device, typically includes a base body, an elastomeric sealing ring, an annular body which can be connected to the base body and a grip ring which locks in position a pipe end inserted into the push-fit fitting device. A grip ring typically enables smooth insertion of a pipe into the fitting device but disallows the removal of the pipe from the fitting device. The grip ring of the present invention provides an improved locking mechanism that enables a continuous mechanical gripping of a pipe end, pushed into the push-fit fitting device. The sealing ring enables a hermetic sealing of the mechanical joint made with at least one pipe end, indifference of the materials the pipes are made of, whether metallic or non-metallic.

Many mechanical jointing applications are used in pipe systems carrying liquids at temperatures up to about 110° C. and higher, and pressures up to approximately 1000 psi. Furthermore, coupling devices of this type are typically used with water pipe systems but can also used with fluids of all types, including toxic and volatile chemicals.

To withstand different pressures, pipes are made of different thicknesses. Typically the external diameter of water pipes is constant, and the thickness varies inwardly, towards the longitudinal axis of the pipe. To differentiate between the pipes, having the same external diameter, the pipes typically are manufactured with different colors, whereas each internal diameter is represented by a given color.

There is a further need for, and it would be advantageous to have, a push-fit fitting device having ring sealers that provide sealing of the mechanical joints between the push-fit fitting device and the inserted pipe, and grip rings, such as provided by PCT application PCT/IL2008/001480, that lock the inserted pipe in an increased force and increases the grip locking force when the inserted pipe attempts to move out of the fitting device.

SUMMARY OF THE INVENTION

The principal intentions of the present invention include proving push-fit pipe fitting devices and in particularly for push-fit pipe fitting devices, the fitting device including a body, a pipe insert, a nut, a ring sealer and a grip ring at each end of the fitting device.

Generally, the push-fit pipe fitting devices of the present invention will be described in terms of a fitting device that couples to two pipes, but the pipe fitting devices of the present invention are not limited to coupling two pipes and the push-fit pipe fitting devices may come in various fitting configurations including the coupling of three pipes, four pipes or any other number of pipes.

According to the teachings of the present invention there is provided a push-fit pipe fitting device assembly, according to embodiments of the present invention. The push-fit pipe fitting device connects at least two pipes, whereas after connection, the tangential longitudinal axis of the pipe fitting device is substantially tangential longitudinal axes of the pipes. The push-fit pipe fitting device assembly includes a main body, a tubular insert, a nut having a wide end and a narrow end, a grip ring having a wide end and a narrow end, and one or more elastomeric sealing rings.

The main body includes one or more tubular portions having a first end, a second end and a longitudinal axis. Typically, with no limitation on the number of tubular portions, the main body includes two tubular portions forming a single tubular body. The first end of each of the tubular portions is rigidly connected either to a first end of another tubular portion or to another plumbing connecting means, such as standard thread. Each of the second ends of the tubular portions is an open end, designed to host a pipe, which is to be inserted through the second end of the tubular portion.

The tubular insert includes two portions, having a first end of and a second end. The tubular insert is fittingly disposed inside each of the tubular portions of the main body. The nut having a wide end and a narrow end is fittingly disposed over, each of the second ends of the main body. The grip ring is fittingly disposed over each of the second ends of the tubular portions, and inside the nut. The one or more elastomeric sealing rings are fittingly disposed at each end of the tubular inserts.

An aspect of the present invention is to provide a push-fit pipe fitting device assembly, wherein when the fitting device is assembled, the sealing rings are fittingly disposed in respective grooves approximately at the ends of each of the tubular inserts. The first portion of each of the tubular inserts is respectively inserted into the internal space of the main body, through the second end of the tubular portion of the main body, and thereby sealingly locking the tubular insert into the main body. The grip rings are then loosely disposed over the second portion of each of the tubular insert. The wide end of each of the nut is respectively inserted over the grip ring and forcefully locking onto a radially fitted nut-locking-mechanism, disposed on the external surface of the main body. The narrow end of each of the nuts is smaller in diameter than the narrow end of the respective grip ring, thereby locking the grip ring inside the fitting device assembly. The narrow end of each of the nuts is larger in diameter than the second portion of the respective tubular inserts.

According to further teachings of the present invention the grip ring further include an annular body, a cylindrical inner surface, an external surface having a conical like structure, a slit cut through the annular body, extending from the narrow end to the wide end, and at least one annular gripping tooth disposed on the inner surface of the grip ring. The smaller most diameter of the annular gripping tooth, the grip ring being in a non compressed state, is smaller than the external diameter of the inserted pipe.

According to further teachings of the present invention, each of the tubular inserts further includes an inner surface, an external surface, a pipe stopper, one or more grip ring stoppers disposed on the pipe stopper, and one or more annular teeth disposed at the second end of the second portion of the tubular insert. The pipe stopper separates the first and second portions of the tubular insert, wherein the pipe stopper extends outwardly substantially perpendicular to the external surface of the tubular insert. The one or more grip ring stoppers, disposed on the pipe stopper, extend substantially perpendicular to the pipe stopper and substantially parallel to the external surface of the tubular insert, towards the second end of the second portion of the tubular insert.

An aspect of the present invention is to provide a push-fit pipe fitting device assembly, wherein when the pipe is forcefully inserted into the end of the fitting device, the internal surface of the pipe slides over the second end of the second portion of the tubular insert and over the one or more sealing rings disposed at the second end of the second portion of the tubular insert, thereby obtaining a full sealing of the inside of the pipe. As the pipe continues to move in, the pipe pushes the grip ring until the grip ring is stopped by the grip ring stopper. As the pipe continues to move in, the external surface of the pipe slides over the at least one annular gripping tooth of the grip ring and expands the longitudinal opening of the grip ring with respect to the longitudinal axis of the pipe. The pipe proceeds to move in until the rim of the pipe reaches the pipe stopper. The annular teeth, disposed at the second end of the second portion of the tubular insert, penetrate into the internal surface of the pipe, thereby grip the pipe.

An aspect of the present invention is to provide a push-fit pipe fitting device assembly, wherein after the pipe has reached the stopper of each of the tubular segment of the fitting device, when a forceful outward movement is applied to one of the pipes with respect to the other pipes, the forceful outward movement activates the gripping operation of the fitting device assembly.

The gripping operation of the fitting device assembly of the present invention includes the steps of:
 a) the conical external surface of the grip ring encounters an inner conical surface of a respective nut;
 b) the inner conical surface of the nut pushes the grip ring inwardly towards the longitudinal axis of the pipe, and thereby compressing the grip ring; and
 c) at least one of the annular gripping tooth move forcefully inwardly towards the longitudinal axis of the pipe, thereby the annular gripping tooth penetrates into the external surface of the pipe, and thereby strengthening the grip on the pipe.

It should be noted that the grip ring and the tubular insert form a U-shaped assembly, wherein said U-shaped assembly grips the pipe about the rim of the pipe, wherein the rim of the pipe is disposed inside the U-shaped assembly.

It should be noted that the diameter of the external surface of the tubular insert, the internal diameter of the grip ring and the inner diameter of the opening of the narrow of end of the nut are designed to match the external diameter of the pipe.

In variations of the present invention, two or more of the second ends of the main body are designed to grip pipes with different external diameter.

In variations of the present invention, at least one of the elements of the push-fit pipe fitting device assembly are selected from the group consisting of a tubular insert, a grip ring and a nut, has a color representing the external diameter of the target pipe.

According to further teachings of the present invention, each of the nuts further includes multiple windows and multiple slits extending from the rim of the wide end towards the narrow end, not reaching said narrow end, thereby forming bendable portions between two adjacent slits. In variations of the present invention, the length of the slits is less than half the distance from the wide end to the narrow end.

According to further teachings of the present invention, the nut-locking-mechanism includes protrusions extending from the external surface of the main body. When the rim of the wide end of the nut reaches the protrusions, the bendable portions bend outwardly, with respect to the longitudinal axis of the fitting device, thereby sliding over the protrusions/when the windows reach their respective protrusions, the bendable portions bend back inwardly, with respect to the longitudinal axis of the fitting device, thereby locking the windows over the protrusions and thereby locking the nut onto the main body.

It should be noted that the external contour of the external surface of the main body, where the nut-locking-mechanism is disposed, forms a radially symmetric polygon-like shape, the cross section plane of the external contour being perpendicular to the longitudinal axis of the fitting device.

It should be further noted that the internal contour of the internal surface of the nut, where said windows are disposed, forms a radially symmetric polygon-like shape, the cross section plane of the internal contour being perpendicular to the longitudinal axis of the fitting device. The internal contour of the internal surface of the nut is designed to match the external contour of the external surface of the main body, where the nut-locking-mechanism is disposed, and thereby preventing radial movement of the nut with respect to the main body.

It should be further noted that the alignment between the external surface of the main body with the internal surface of the nut, brings the windows to locking alignment with the protrusions.

According to further teachings of the present invention, the main body further includes ribs extending from each of the second ends of the main body. The external surface of each of the ribs substantially coincides with the corresponding side of the polygon-like external contour of the external surface of the main body. The internal contour of the ribs, the cross section plane of the internal contour being perpendicular to the longitudinal axis of the fitting device, forms a radially asymmetric polygon-like shape.

The external contour of the pipe stopper of the tubular insert forms a radially asymmetric polygon-like shape, wherein the internal contour of the internal surface of the ribs is designed to match the external contour of the pipe stopper, preventing radial movement of the tubular insert with respect to the main body. The asymmetric contour of the pipe stopper, that directionally guides the insert during insertion of the pipe, ensures that the pipe stopper supporting ribs do not obstruct the windows of the nut or the gaps between the ribs of the main body.

An aspect of the present invention is to provide a push-fit pipe fitting device assembly, wherein the hardness of the materials from which the gripping teeth of the grip ring and the gripping teeth of the tubular insert are made, is greater than the hardness of the material from which the pipe is made.

It should be noted that the tubular insert can be viewed while and after the pipe is inserted into the fitting device assembly.

It should be further noted that the pipe can be viewed while and after the pipe is inserted into the fitting device assembly.

BRIEF DESCRIPTION OF THE DRAWINGS

The present invention will become fully understood from the detailed description given herein below and the accompanying drawings, which are given by way of illustration and example only and thus not limitative of the present invention, and wherein:

FIGS. 2a and 2b are perspective view illustrations of the push-fit pipe fitting device assembly shown in FIG. 1, having two pipes being pushed into the fitting device.

FIG. 5 is an exploded side view illustration of the push-fit pipe fitting device assembly shown in FIG. 1.

FIG. 6 is a side view illustration of the push-fit pipe fitting device assembly shown in FIG. 1, having one side assembled and the other side in an exploded view.

FIG. 7 is a side view illustration of the push-fit pipe fitting device assembly shown in FIG. 6, wherein the ring sealers are assembled.

FIG. 8 is a front view illustration of the main body of the push-fit pipe fitting device assembly shown in FIG. 1.

FIG. 9 is a side perspective view illustration of the push-fit pipe fitting device assembly shown in FIG. 7.

FIG. 10 is a side perspective view illustration of the push-fit pipe fitting device assembly shown in FIG. 7, wherein the pipe insert is fully inserted into the main body of the push-fit pipe fitting device assembly.

DETAILED DESCRIPTION OF THE PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided, so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The methods and examples provided herein are illustrative only and not intended to be limiting.

By way of introduction, the principal intentions of the present invention include proving push-fit pipe fitting device assemblies designed to connect and seal pipes, in a pressurized system, typically a water pipe system, for either cold or hot water. The push-fit pipe fitting device assembly will be described in terms of being designed to connect and seal two pipes, but the push-fit pipe fitting device assembly of the present invention is not limited to connecting just two pipes, and can be designed to connect any number of plastic pipes. The pipes for which the push-fit pipe fitting device assembly of the present invention is designed to connect and seal are typically, but not exclusively, plastic pipes.

Figure 1:
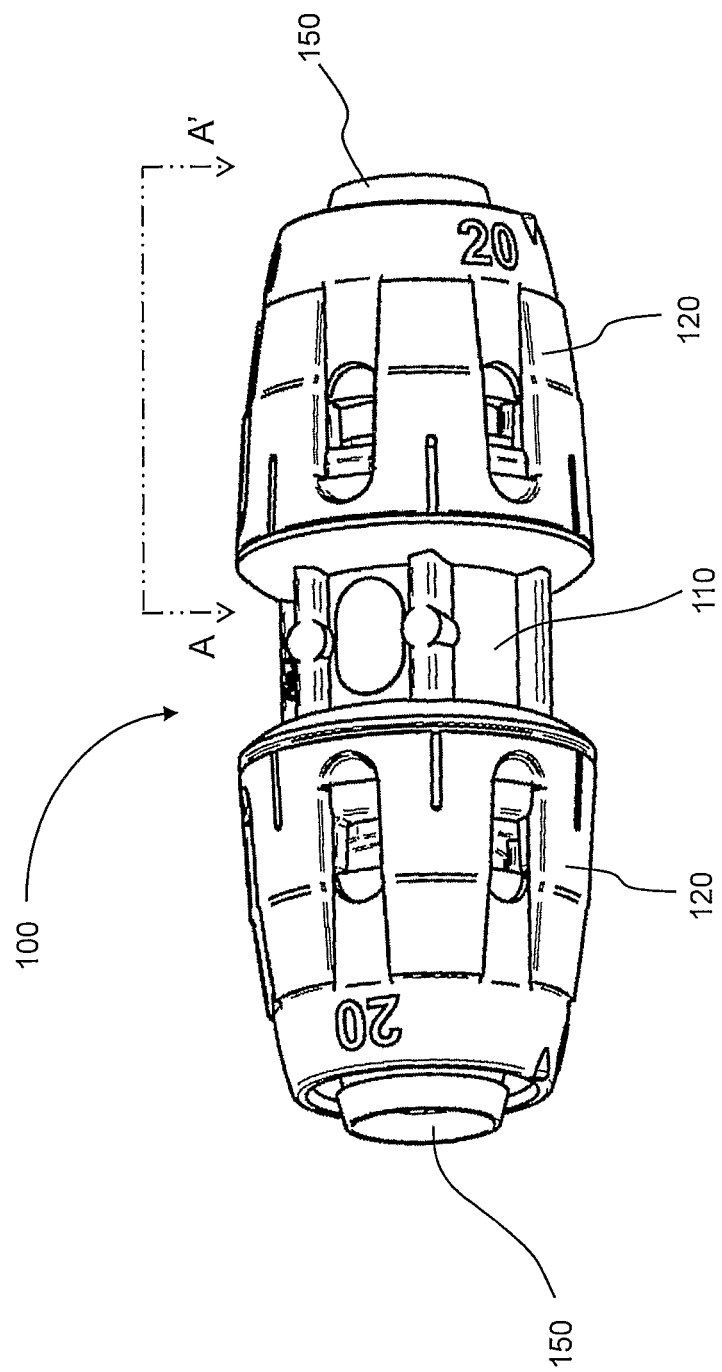
FIG. 1 is a side view illustration of a push-fit pipe fitting device assembly, according to embodiments of the present invention.

Reference is now made to the drawings. FIG. 1 is a side view illustration of push-fit pipe fitting device assembly 100, according to embodiments of the present invention. Fitting device 100 includes main body 110, pipe insert 150, two nuts 120, two grip rings 130 and four ring sealers 140. FIG. 2 is a perspective view illustration of push-fit pipe fitting device assembly 100, having two pipes (50a, 50b) being respectively pushed into each end of fitting device 100.

Figure 4:
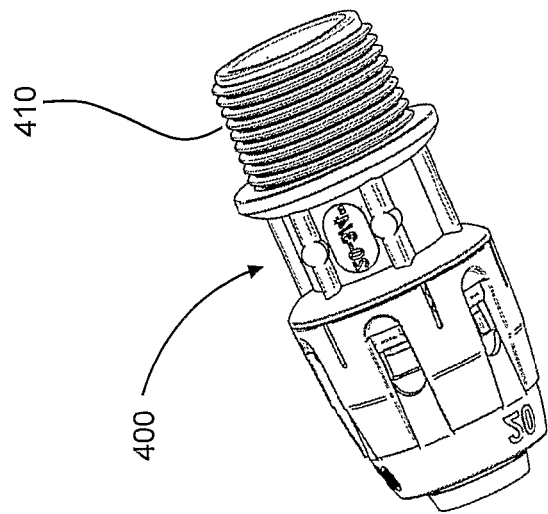
FIG. 4 is a side view illustration of a push-fit pipe fitting device assembly, according to embodiments of the present invention, wherein the fitting device assembly is designed to push-fit-connect one pipe.
Figure 3:
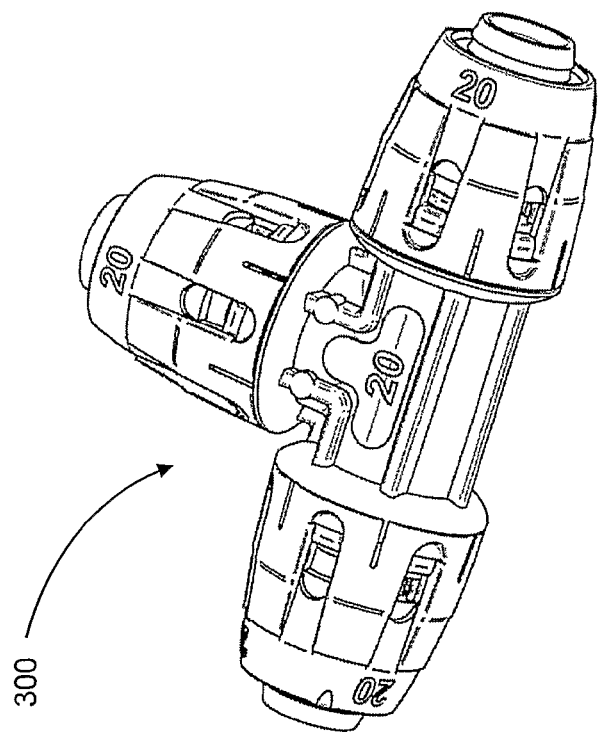
FIG. 3 is a side view illustration of a push-fit pipe fitting device assembly, according to embodiments of the present invention, wherein the fitting device assembly is designed to push-fit-connect three pipes.

By way of example, with no limitation upon other variations of the present inventions, the present invention will be now described primarily through push-fit pipe fitting device assemblies for connecting two pipes. But the present invention is not limited to push-fit pipe fitting device assembly for connecting two pipes, and in other variations of the present invention the push-fit pipe fitting device assembly can connect any number of pipes. For example, FIG. 3 is a perspective view illustration of push-fit pipe fitting device assembly 300 for connecting three pipes. In another example, FIG. 4 is a perspective view illustration of push-fit pipe fitting device assembly 400 for connecting one pipe, while on the other side another conventional plumbing unit can be attached onto a prior art plumbing connecting means such as threads 410.

Reference is also made to FIGS. 5-12: FIG. 5 is an exploded side view illustration of fitting device 100; FIG. 6 is a side view illustration of fitting device 100, having one side assembled and the other side in an exploded view; FIG. 7 is a side view illustration of fitting device 100, wherein ring sealers 140 are assembled; FIG. 8 is a front view illustration of main body 110 of push-fit pipe fitting device 100; FIG. 9 is a side perspective view illustration of fitting device 100; FIG.

Figure 11:
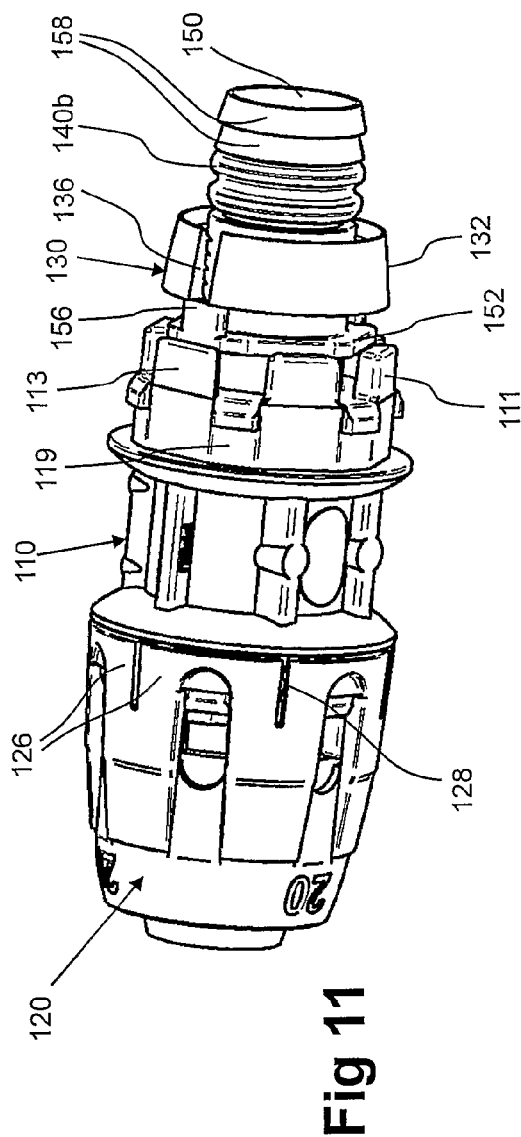
FIG. 11 is a side view illustration of the push-fit pipe fitting device assembly shown in FIG. 7, wherein the pipe insert, including a grip ring, is partially inserted into the main body of the push-fit pipe fitting device assembly.
Figure 12:
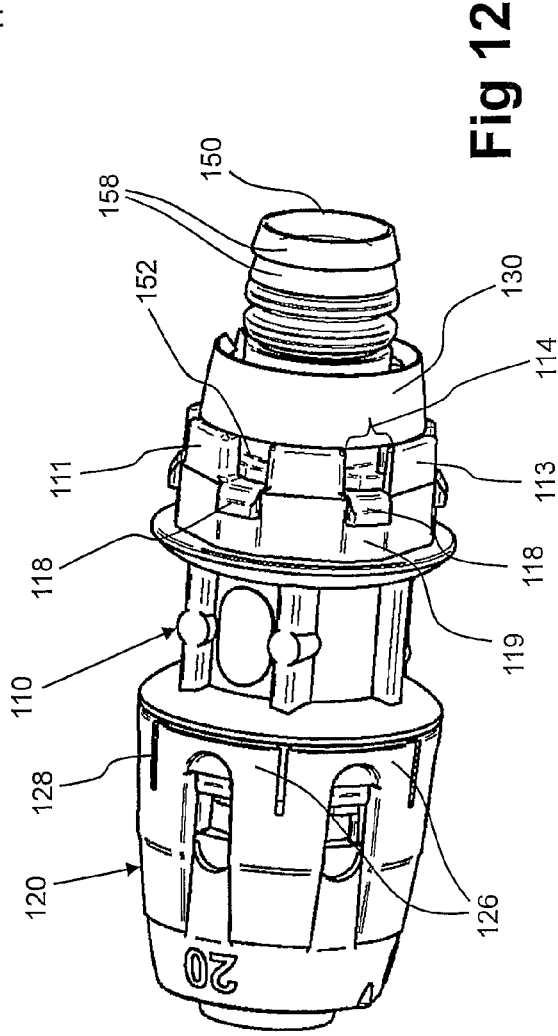
FIG. 12 is a side view illustration of the push-fit pipe fitting device assembly shown in FIG. 7, wherein the pipe insert, including a grip ring, is fully inserted into the main body of the push-fit pipe fitting device assembly.

10 is a side perspective view illustration of fitting device 100, wherein tubular insert 150 is fully inserted into main body 110; FIG. 11 is a side view illustration of fitting device 100, wherein tubular insert 150, including grip ring 130, is partially inserted into main body 110; and FIG. 12 is a side view illustration of fitting device 100, wherein tubular insert 150, including grip ring 130, is fully inserted into main body 110.

Main body 110 is the interface part that symmetrically connects with identical mechanisms the two pipes. The symmetry can be broken only when fitting pipes of different diameters, whereas on the diameters of respective parts differ on both sides of main body 110. The description will hereon be in terms of connecting a pipe to one side of main body 110, wherein the same is applied to the other side of main body 110.

Main body 110 includes an inner opening 117 (FIGS. 8, 9) into which tubular insert 150 is inserted. Main body 110 further includes a ribbed structure which includes ribs 112 having gap 114 between adjacent ribs, and protrusions 118, whereas each protrusion 118 is disposed on to outer surface of the ribs structure, behind each gap 114. Ribs 112 include thin ribs 113 and thick ribs 111; whereas ribs 112 form a polygon-like radial symmetric external contour 115 and a polygon-like radial asymmetrical inner contour 116, as illustrated in FIG. 8. In the example shown in the figures, main body 110 includes a ribs structure which includes 6 ribs 112 generally forming a hexagon structure. It should be noted the contours refer to the contour formed by a cross section plane perpendicular to longitudinal axis 105 of fitting device 100.

Tubular insert 150 includes annular ribs 154 (FIG. 6), on which corresponding grooves in ring sealers 140 are disposed, stopper 152 and annular teeth 158, disposed on the end of tubular insert 150 that is opposite to the side of main body 110. Stopper 152 includes supporting ribs 156 that protrude out of stopper 152. The external contour of stopper 152 fits inner contour 116 of the ribs structure of main body 110, and since the contours are asymmetric, the insertion of tubular insert 150 inside the ribs structure of main body 110 becomes directionally dictated. The position of supporting ribs 156 on stopper 152 coincide with the position of thin ribs 113 on the ribs structure of main body 110. The width of supporting ribs 156 is not larger than the width of thin ribs 113, and the ribs structure of stopper 152 does not allow supporting ribs 156 to block gap 114.

Grip ring 130 has an annular structure, whereas in a longitudinal cross section of grip ring 130, external surface 132 of the grip ring 130 has a conical like structure. On the inner surface of grip ring 130 multiple annular gripping teeth 134 are disposed. Annular grip ring 130 needs to be radially deformable and gap 136 allows grip ring 130 to be compressed.

Figure 13:
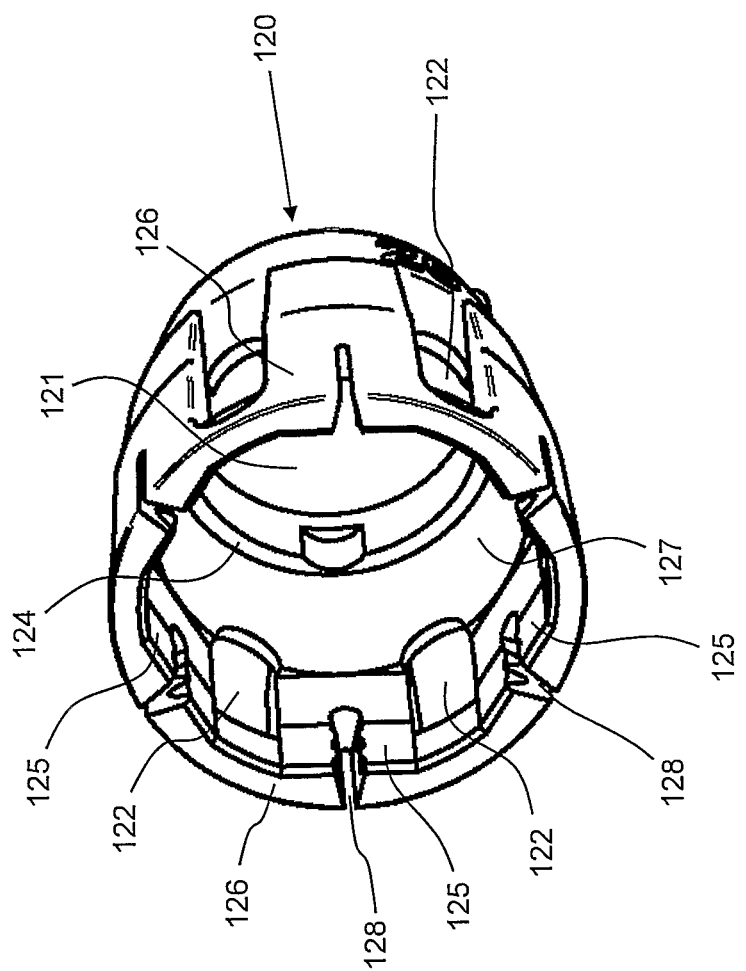
FIG. 13 is a side perspective view illustrations of the nut of the push-fit pipe fitting device assembly shown in FIG. 1.

Reference is also made to FIG. 13, which is a side perspective view illustrations of nut 120 of push-fit pipe fitting device assembly 100. Nut 120, includes an external conical surface, internal surfaces 125, an internal conical surface 127, windows 122, a step stopper 124, opening 121 into which a pipe is inserted, slits 128 and portions 126 disposed between slits 128. Slits 128 enable each portion 126 to bend individually, nut 120 being made of materials with the required elasticity. Internal surfaces 125 form a radial contour that fits external contour 115 (FIGS. 8, 9) formed by the external surfaces of ribs 112. Windows 122 are disposed between adjacent surfaces 125. The inclination angle and position of conical surface 127 matches the inclination angle of external surface 132 of grip ring 130.

The assembly of all sides of push-fit pipe fitting device assembly 100 is similar and hence the hereon assembly description of one side of fitting device 100 applies to all sides. The assembly starts by disposing ring sealers 140 onto tubular insert 150, whereas tubular insert 150 includes two pairs of annular ribs 154 (FIG. 6), one on each side of tubular insert 150, on which corresponding grooves in ring sealers 140 are disposed (FIG. 7).

It should be noted that ring sealer 140 is the preferred ring sealer of the present invention, but the present invention is not limited to ring sealer 140 and any ring sealer (or combination of ring sealers) can be used, providing corresponding adjustments to tubular insert 150 are made.

Figure 14:
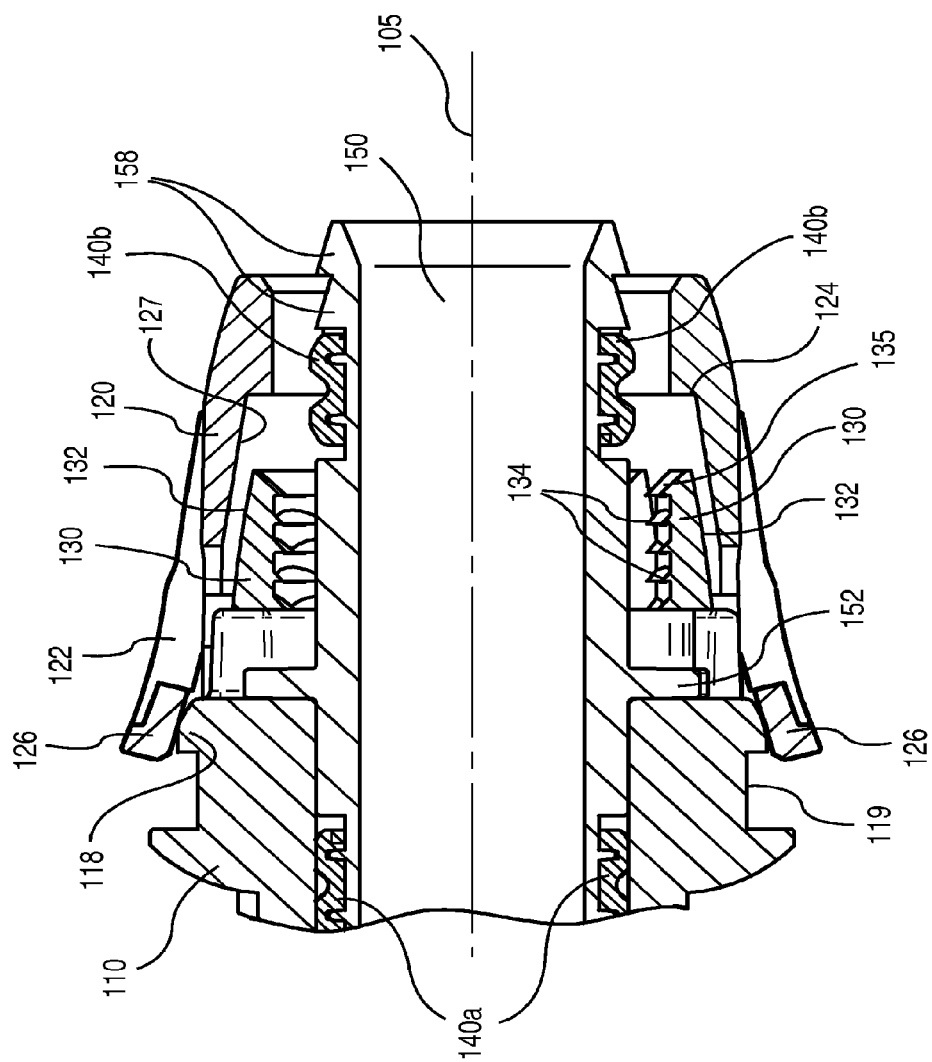
FIG. 14 is cross section AA' broken view illustration of the end of the push-fit pipe fitting device assembly shown in FIG. 1, being fully assembled.
Figure 15:
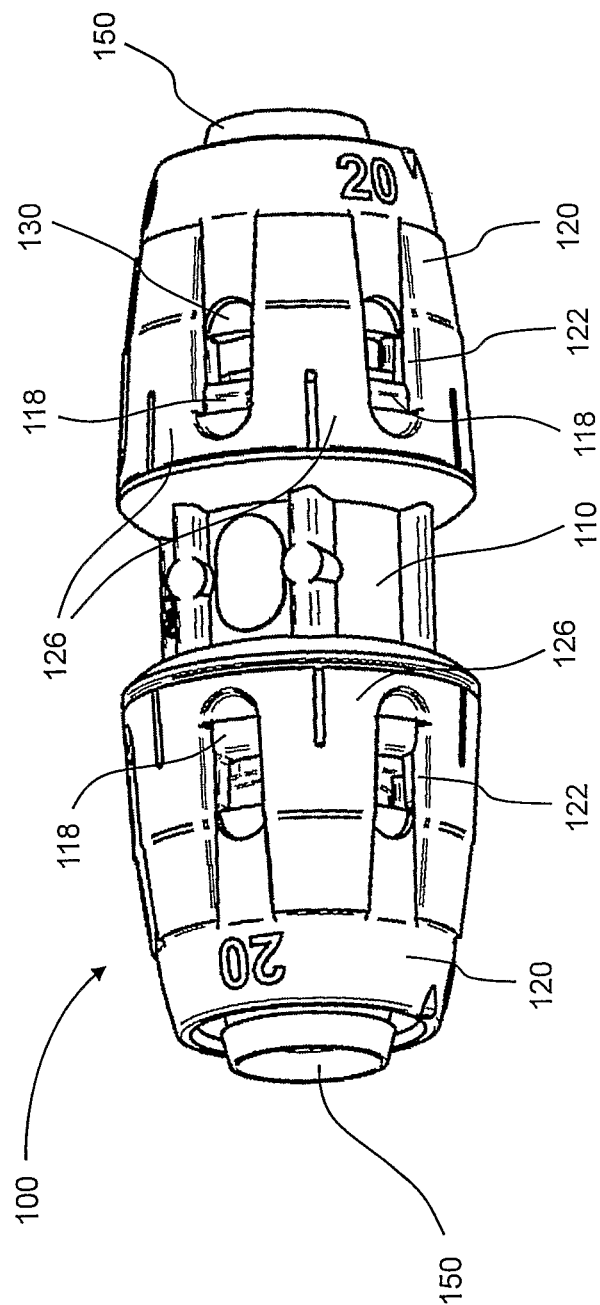
FIG. 15 is a side view illustration of the push-fit pipe fitting device assembly shown in FIG. 1, being fully assembled.

Reference is also made to FIG. 14, which is cross section AA' (FIG. 1) broken view illustration of the end of push-fit pipe fitting device assembly 100, being fully assembled, and to FIG. 15, which is a side view illustration of fitting device 100, being fully assembled.

Tubular insert 150 is then inserted into opening 117 in main body 110 (FIGS. 9 and 10) wherein ring sealer 140a seals tubular insert 150 inside main body 110 (FIG. 14). The shape of the external contour of stopper 152 fits inner contour 116 of the ribs structure of main body 110, and since both contours are asymmetric, the insertion of tubular insert 150 inside the ribs structure of main body 110 is directionally dictated, and any relative rotational movement between tubular insert 150 and main body 110 is prevented. The position of supporting ribs 156 on stopper 152 coincide with the position of thin ribs 113 on the ribs structure of main body 110, and gaps 114 remain open.

Grip ring 130 is then passed over the open end of tubular insert 150 having the wider side of grip ring 130 facing main body 110. Following grip ring 130, nut 120 is then passed over the open end of tubular insert 150, and forcefully pushed onto protrusion 118 of main body 110. The movement of grip ring 130 is stopped by ribs 112. Inner surfaces 125 of nut 120 internal surfaces 125, having a contour that fits external contour 115 formed by the external surfaces of ribs 112, directionally guide the insertion of nut 120 onto the ribs structure of main body 110. When portions 126 disposed between slits 128 of nut 120 reach protrusions 118 of main body 110, portions 126 slightly bend outwards, with respect to longitudinal axis 105 of fitting device 100 (see FIG. 14), slide over protrusions 118 and when windows 122 pass over protrusions 118, portions 126 bend back towards surface 119 of main body 110, thereby locking nut 120 to main body 110. Tubular insert 150 still has the freedom to move a few millimeters inside main body 110, along longitudinal axis 105 of fitting device 100.

Figure 16A:
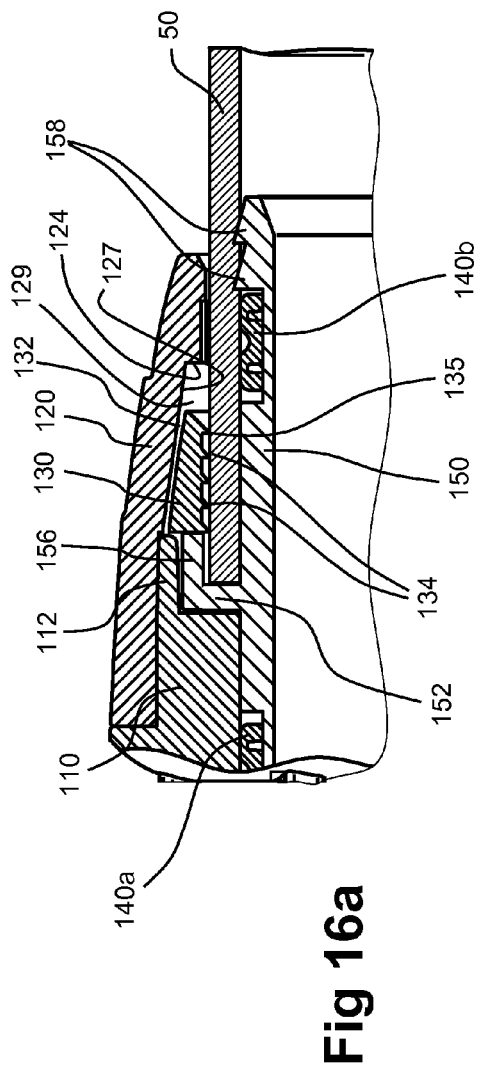
FIG. 16a is a cross section, broken view illustration of a portion of the end the push-fit pipe fitting device assembly shown in FIG. 1, being fully assembled with a pipe.
Figure 17A:
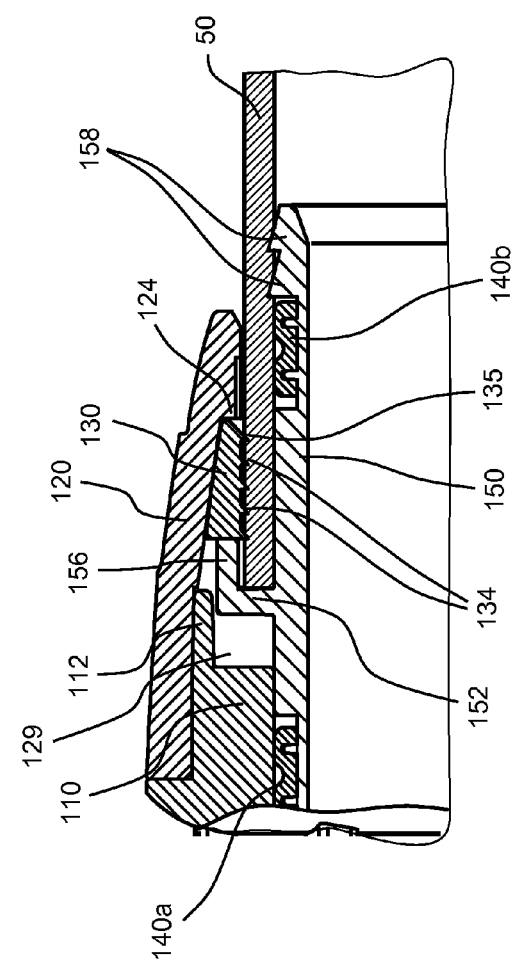
FIG. 17a is a cross section, broken view illustration of the portion of the end the push-fit pipe fitting device assembly shown in FIG. 16a, wherein the pipe has been pulled.
Figure 18:
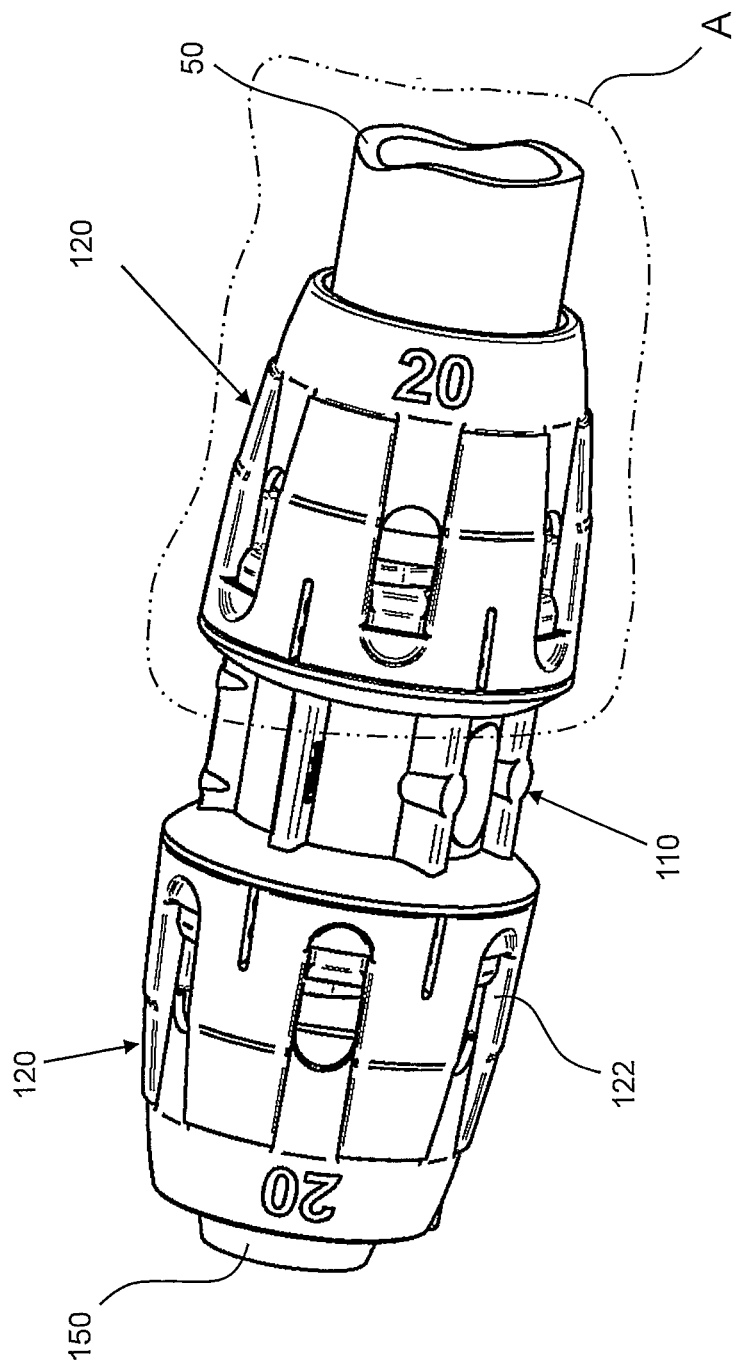
FIG. 18 is a side view illustration of the push-fit pipe fitting device assembly shown in FIG. 1, being fully assembled, including a pipe inserted into the fitting device.
Figure 19:
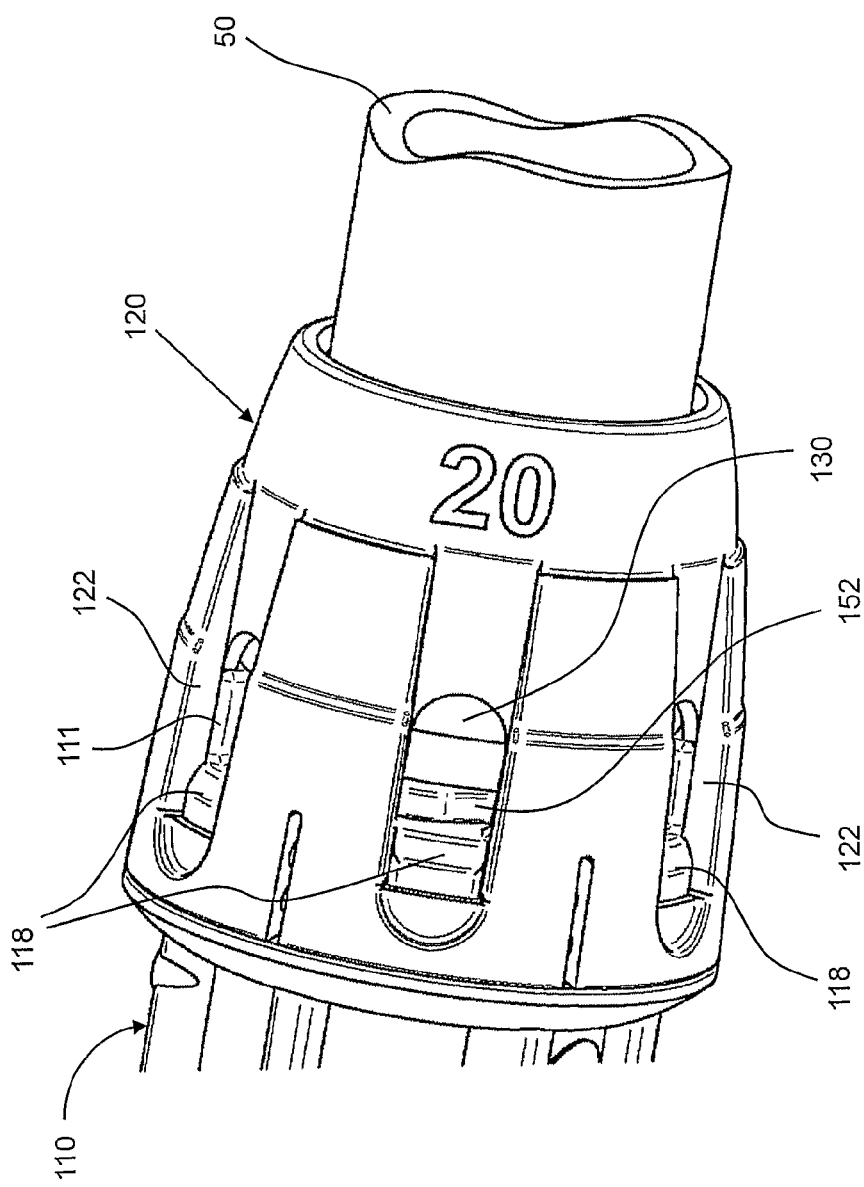
FIG. 19 is a detailed view of window "A" shown in FIG. 18.

Reference is also made to FIGS. 16a-19: FIG. 16a is a cross section, broken view illustration of a portion of fitting device 100, being fully assembled with a pipe; FIG. 17a is a cross section, broken view illustration of the portion of the end fitting device 100 as shown in FIG. 16a, wherein the pipe has been pulled; FIG. 18 is a side view illustration of fitting device 100, being fully assembled, including inserted pipe 50; and FIG. 19 is a detailed view of window "A" shown in FIG. 18.

Figure 16B:
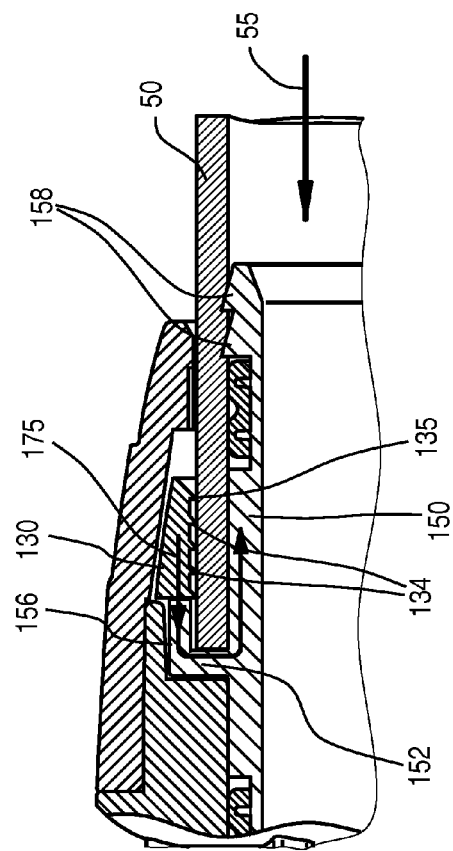
FIG. 16b illustrates forces relations between the grip ring and the pipe insert, when the pipe is pushed into the push-fit pipe fitting device assembly shown in FIG. 1.
Figure 17B:
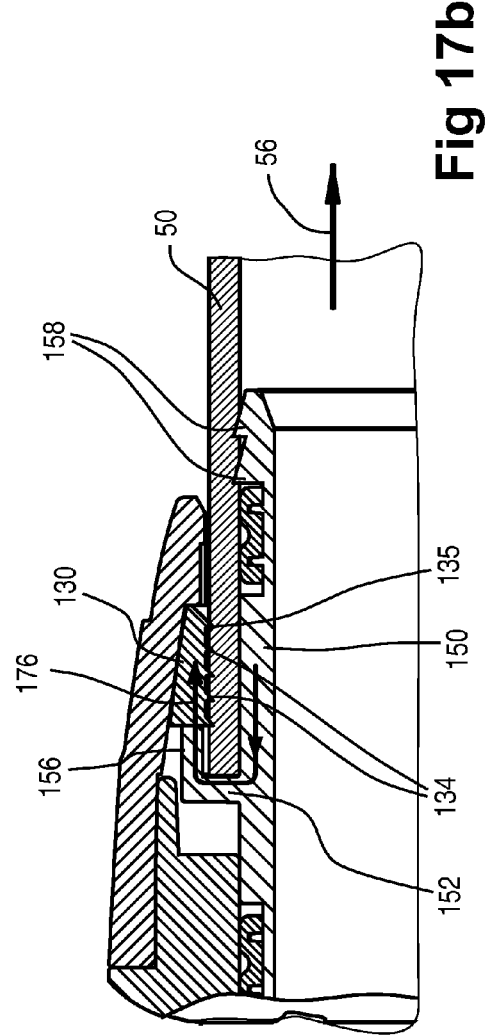
FIG. 17b illustrates forces relations between the grip ring and the pipe insert, when the pipe is pulled out of the push-fit pipe fitting device assembly shown in FIG. 1.

To attach a pipe to an end of push-fit pipe fitting device 100, pipe 50 of compatible diameter is pushed into the opening at end of fitting device 100. Pipe 50 slides over annular teeth 158 disposed on the end of tubular insert 150, then slides over and squashes ring sealer 140b, thereby obtaining a full sealing of the inside of pipe 50. As pipe 50 continues to move in, the external surface of pipe 50 reaches gripping teeth 134 of grip ring 130, slides over the first gripping tooth 135 and expands gap 136 of grip ring 130 and thereby expand the radius of grip ring 130. Pipe 50 proceeds moving in sliding over gripping teeth 134 until the rim of pipe 50 reaches stopper 152. As pipe 50 slides into pipe fitting device 100, pipe 50 can be viewed and monitored through windows 122. Reference is also made to FIG. 16b, which illustrates forces relations between grip ring 130 and tubular insert 150, when pipe 50 is pushed into the push-fit pipe fitting device 100, and to FIG. 17b, which illustrates forces relations between grip ring 130 and tubular insert 150, when pipe 50 is pulled out of push-fit pipe fitting device 100. When pipe 50 is pushed into fitting device 100, in direction 55, forces convey from grip ring 130 towards tubular insert 150, in direction 175. When pipe 50 is pulled out of fitting device 100, in direction 56, forces convey from tubular insert 150 towards grip ring 130, in direction 176.

As pipe 50 reaches stopper 152, annular teeth 158 penetrate into the internal surface of pipe 50 (FIG. 16a). When pipe 50 is pulled outwardly from fitting device 100, annular teeth 158 further penetrate into the internal surface of pipe 50 (FIG. 17a) and in turn, pipe 50 pulls tubular insert 150 outwardly from fitting device 100. When supporting ribs 156 of tubular insert 150 reach grip ring 130, which moves along with tubular insert 150 until external surface 132 of grip ring 130 reaches internal surface 127 of nut 120. Surface 127 pushes external surface 132 inwardly, thereby forcing grip ring 130 to slightly close gap 136 (FIGS. 7, 11) of grip ring 130, and thereby gripping teeth 134 further penetrate into the external surface of pipe 50. Hence, pipe 50 is now held by annular teeth 158, gripping the internal surface of pipe 50 and by gripping teeth 134, gripping the external surface of pipe 50.

As pipe 50 is being further pulled outwardly from fitting device 100, annular teeth 158 and gripping teeth 134 further penetrate into surface of pipe 50, while grip ring 130, may further move outwardly as the diameter of grip ring 130 gets smaller. Grip ring 130 may reach a final stop when reaching stopper step 124.

It should be noted that through out the push/pull processes of pipe 50 in/out of fitting device 100, tubular insert 150 can be viewed through windows 122, including stopper 152.

Figure 20:
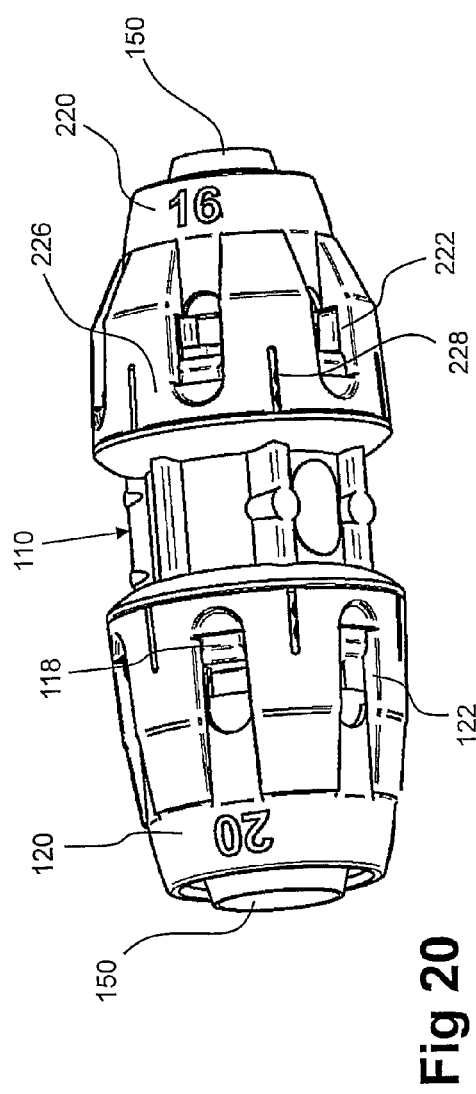
FIG. 20 is a side view illustration of the push-fit pipe fitting device assembly, according to embodiments of the present invention, wherein each side is designed for a different pipe diameter size.
Figure 21:
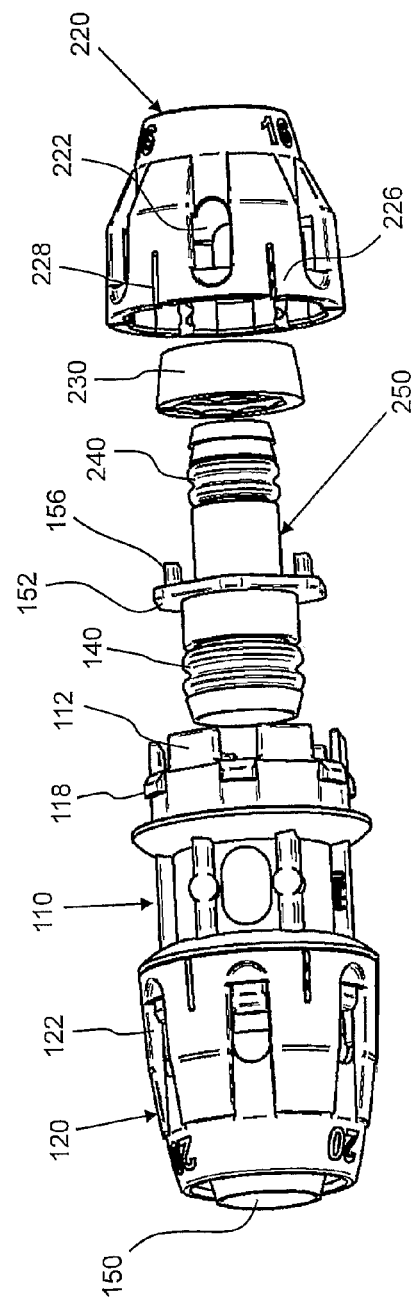
FIG. 21 is a side view illustration of the push-fit pipe fitting device assembly shown in FIG. 20, having one side assembled and the other side in an exploded view.

Since typically the external diameter of water pipes is constant, and the thickness of the pipe varies inwardly, towards the longitudinal axis of the pipe, tubular inserts are provided by the present invention, wherein pipes of different diameters can be connected by a single tubular insert. Reference is now made to FIG. 20, which is a side view illustration of push-fit pipe fitting device assembly 200, according to embodiments of the present invention, wherein each side of fitting device 200 is designed for a different pipe diameter size, and to FIG. 21, which is a side view illustration of fitting device 200, having one side assembled and the other side in an exploded view. Referring also back to FIG. 2, while in device 100 diameter D of pipe 50a is substantially the same as diameter D of pipe 50b, in device 200, diameter D of pipe 50a differs from diameter D of pipe 50b.

In embodiments of the present invention, tubular inserts that are designed to fit a different combination of pipe sizes, are fabricated in a different color.

Hence to know the size of each end of a particular tubular insert (150, 250), one can either measure the diameter of each end of that tubular insert (150, 250), or interpret the tubular insert color. When assembled inside a push-fit pipe fitting device (100, 200) of the present invention, the color of a tubular insert (150, 250) can also be viewed through windows (122, 222).

It should be noted that to change the size of a pipe on either end of pipe fitting device 100, only corresponding tubular insert 250, grip ring 230 and corresponding nut 220 need to be replaced.

In embodiments of the present invention, the size of the nut is imprinted or molded on the external surface of the nut. For example, nut 120 of pipe fitting device 100 fit pipes 50b, having a 20 mm internal diameter, and nut 220 of pipe fitting device 200 fit pipes 50a, having a 16 mm internal diameter.

The invention being thus described in terms of several embodiments and examples, it will be obvious that the same may be varied in many ways. Such variations are not to be regarded as a departure from the spirit and scope of the invention, and all such modifications as would be obvious to one skilled in the art.

What is claimed is:

1. A push-fit pipe fitting device assembly for connecting one or more pipes, each of said pipes having a longitudinal axis, the fitting device assembly comprising:
   a main body comprising one or more tubular portions, each of the one or more tubular portions having a first end, a second end and a longitudinal axis; wherein said first end of each of said tubular portions is rigidly connected either to a first end of another tubular portion or to a connecting device that connects the one or more pipes to a pipe system; wherein each of said second ends of said tubular portions is an open end; and wherein each of said second ends of said tubular portions is configured to host one of said pipes within said second end of said tubular portions;
   one or more tubular inserts, each tubular insert comprising a first end and a second end, wherein said one or more tubular inserts are fittingly disposed inside each of said tubular portions of said main body;
   one or more nuts, each nut having a wide end and a narrow end, wherein one of said one or more nuts is fittingly disposed over each of said second ends of said main body;
   one or more grip rings, each grip ring having a wide end and a narrow end, wherein one of said one or more grip rings are fittingly disposed over each of said second ends of said tubular inserts, and inside one of said one or more nuts; and
   one or more elastomeric sealing rings fittingly disposed at each end of said one or more tubular inserts,
   wherein each of said grip rings further comprises:
      a cylindrical inner surface; and
      at least one annular gripping tooth disposed on said inner surface; and
   wherein each of said tubular inserts further comprises one or more annular teeth disposed at said second end of said tubular insert;
   wherein said sealing rings are fittingly disposed in respective grooves at approximately said ends of each of said tubular inserts;
   wherein said first portion of each of said tubular inserts is respectively inserted into an internal space of said main body, through said second end of each of said tubular portion of said main body;
   wherein said grip rings are disposed over said second end of each of said tubular insert;
   wherein said wide end of each of said nuts is respectively inserted over said grip ring and locked onto a radially fitted nut-locking-mechanism formed from the external surface of said main body,
   wherein said narrow end of each of said nuts is smaller in diameter than said narrow end of said respective grip ring, thereby locking said grip ring inside said fitting device assembly, and
   wherein said narrow end of each of said nut is larger in diameter than said second end of said respective tubular inserts; and wherein the push-fit pipe fitting is connectable to the one or more pipes such that each of the one or more tubular portions has a pipe of the one or more pipes inserted therein, wherein each of said grip rings further comprises:
an annular body;
an external surface having a substantially conical shape;
a slit cut through said annular body, extending from said narrow end to said wide end;
wherein the smaller most diameter of said at least one annular gripping tooth, said grip ring being in a non compressed state, is smaller than the external diameter of said one or more inserted pipes; and
wherein each of said tubular inserts further comprises:
an inner surface;
an external surface;
a pipe stopper disposed separating said first and second ends of said tubular insert, wherein said pipe stopper extends outwardly substantially perpendicular to said external surface of said tubular insert; and
one or more grip ring stoppers disposed on said pipe stopper, extending substantially perpendicular to said pipe stopper and substantially parallel to said external surface of said tubular insert, towards said second end of said second end of said tubular insert;
wherein each of said nuts further comprises:
multiple slits extending from a rim of said wide end towards said narrow end, not reaching said narrow end, thereby forming bendable portions between two adjacent slits; and
multiple windows;
wherein said nut-locking-mechanism comprises protrusions extending from said external surface of said main body;
wherein the push-fit pipe device assembly is configured such that when said rim of said wide end of said nut reaches said protrusions, said bendable portions bend outwardly, with respect to said longitudinal axis of said fitting device, thereby sliding over said protrusions; and
wherein the push-fit pipe device assembly is configured such that when said windows reach respective said protrusions, said bendable portions bend back inwardly, with respect to said longitudinal axis of said fitting device, thereby locking said windows over said protrusions and thereby locking said nut onto said main body.

2. The push-fit pipe fitting device assembly of claim 1,
wherein the wide end and the narrow end are terminal ends of the nut, and
wherein the length of said slits is less than half the distance from said wide end to said narrow end.

3. The push-fit pipe fitting device assembly of claim 1, wherein the push-fit pipe fitting device assembly is configured such that when said pipe is inserted into the fitting device the hardness of the materials from which gripping teeth of said grip ring and said gripping teeth of said tubular insert are made is greater than the hardness of the material from which said pipe is made.

4. The push-fit pipe fitting device assembly of claim 1, wherein the push-fit pipe fitting device assembly is configured such that said tubular insert is viewable by the naked human eye during and after said pipe is inserted into said fitting device assembly.

5. The push-fit pipe fitting device assembly of claim 1, wherein the push-fit pipe fitting assembly is configured such that said pipe is viewable by the naked human eye during and after said pipe is inserted into said fitting device assembly.

6. The push-fit pipe fitting device assembly of claim 1,
wherein the push-fit pipe fitting device assembly is configured such that when said pipe is inserted into the fitting device, the internal surface of said pipe slides over said second end of said second end of said tubular insert and over said sealing ring disposed at said second end of said second end of said tubular insert, thereby sealing the fitting device to the inside of the pipe;
wherein the push-fit pipe fitting device assembly is configured such that upon contacting the grip ring, said pipe pushes said grip ring until said grip ring is stopped by said grip ring stopper;
wherein the push-fit pipe fitting device assembly is configured such that the external surface of said pipe slides over said at least one annular gripping tooth and expands a longitudinal opening of said grip ring with respect to said longitudinal axis of said pipe; and
wherein the push fit-pipe fitting device assembly is configured such that said pipe is limited from movement when a rim of said pipe reaches said pipe stopper; and
wherein said annular teeth, disposed at said second end of said second end of said tubular insert, penetrate into said internal surface of said pipe.

7. The push-fit pipe fitting device assembly of claim 6, wherein the push-fit pipe fitting device assembly is configured such that when said pipe has reached said stopper of said tubular insert, and when an outward movement force is applied to said pipe, said outward movement force causes the one or more annular teeth and said at least one annular gripping tooth to penetrate into the surface of the pipe.

8. The push-fit pipe fitting device assembly of claim 7, wherein the push-fit pipe fitting device is configured such that during the penetration of the one or more annular teeth and the at least one annular gripping tooth into the surface of the pipe:
said conical external surface of said grip ring encounters an inner conical surface of said respective nut;
said inner conical surface of said nut pushes said grip ring inwardly towards a longitudinal axis of said pipe, and thereby compressing said grip ring; and
said at least one annular gripping tooth move inwardly towards said longitudinal axis of said pipe, thereby said at least one annular gripping tooth of said grip ring penetrates into said external surface of said pipe, and thereby strengthening the grip on said pipe.

9. The push-fit pipe fitting device assembly of claim 8, wherein said grip ring forms a U cross sectionally shaped assembly about said tubular insert, wherein said U cross sectionally shaped assembly grips said pipe about said rim of said pipe.

10. The push-fit pipe fitting device assembly claim 1, wherein the diameter of said external surface of said tubular insert, the internal diameter of said grip ring and the inner diameter of the opening of said narrow end of said nut are selected to fit around an external diameter of said pipe.

11. The push-fit pipe fitting device assembly of claim 8, wherein the push-fit pipe fitting device is configured to connect with two or more pipes having different external diameters.

12. The push-fit pipe fitting device assembly of claim 8, wherein at least one of the elements of said push-fit pipe fitting device assembly are selected from the group consisting of said tubular insert, said grip ring and said nut, has a color corresponding to an external diameter of the pipe.

13. The push-fit pipe fitting device assembly of claim 1, wherein the external contour of said external surface of said main body, where said nut-locking-mechanism is disposed, forms a radially symmetric polygon shape, a cross section plane of said external contour being perpendicular to said longitudinal axis of said fitting device.

14. The push-fit pipe fitting device assembly of claim 13, wherein the internal contour of the internal surface of said nut, where said windows are disposed, forms a radially symmetric polygon shape, a cross section plane of said internal contour being perpendicular to said longitudinal axis of said fitting device, wherein said internal contour of the internal surface of said nut is designed to match said external contour of said external surface of said main body, where said nut-locking-mechanism is disposed, thereby, preventing radial movement of said nut with respect to said main body.

15. The push-fit pipe fitting device assembly of claim 14, wherein the alignment between said external surface of said main body with said internal surface of said nut, brings said windows to locking alignment with said protrusions.

16. The push-fit pipe fitting device assembly of claim 13, wherein said main body further comprises ribs extending from each of said second ends of said main body, wherein the external surface of each of said ribs substantially coincides with the corresponding side of said polygon external contour of said external surface of said main body, and wherein the internal contour of said ribs, a cross section plane of said internal contour being perpendicular to said longitudinal axis of said fitting device, forms a radially asymmetric polygon shape.

17. The push-fit pipe fitting device assembly of claim 16, wherein the external contour of said pipe stopper of said tubular insert, forms a radially asymmetric polygon shape, wherein said internal contour of said internal surface of said ribs is designed to match said external contour of said pipe stopper, preventing radial movement of said tubular insert with respect to said main body.

18. The push-fit pipe fitting device assembly of claim 17, wherein when the asymmetric contour of said pipe stopper, that directionally guides the insert during insertion of said pipe, ensures that said ribs do not obstruct said windows in said nut or gaps located between said ribs of said main body.

* * * * *